United States Patent
Chen et al.

(10) Patent No.: US 8,107,068 B2
(45) Date of Patent: Jan. 31, 2012

(54) RAMAN SPECTROSCOPY SYSTEM AND RAMAN SPECTROSCOPY DETECTION METHOD

(75) Inventors: Zhiqiang Chen, Beijing (CN); Li Zhang, Beijing (CN); Yuanjing Li, Beijing (CN); Yinong Liu, Beijing (CN); Ziran Zhao, Beijing (CN); Mingliang Li, Beijing (CN); Hongfeng Gai, Beijing (CN); Hongqiu Wang, Beijing (CN); Dongmei Yu, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 229 days.

(21) Appl. No.: 12/492,253

(22) Filed: Jun. 26, 2009

(65) Prior Publication Data

US 2009/0323057 A1 Dec. 31, 2009

(30) Foreign Application Priority Data

Jun. 27, 2008 (CN) .......................... 2008 1 0115790

(51) Int. Cl.
*G01J 3/44* (2006.01)
(52) U.S. Cl. ........ 356/301; 356/300; 356/952; 356/953; 707/999.003; 707/E17.014
(58) Field of Classification Search .................. 356/300, 356/301, 952, 953; 707/999.003, E17.014
See application file for complete search history.

(56) References Cited

U.S. PATENT DOCUMENTS

| 5,004,929 | A  | * | 4/1991  | Kakinoki et al. ............. 356/608 |
| 6,313,423 | B1 |   | 11/2001 | Sommer et al. |
| 2005/0162646 | A1 |   | 7/2005  | Tedesco et al. |
| 2005/0206892 | A1 | * | 9/2005  | Wang et al. ................... 356/301 |
| 2005/0248758 | A1 |   | 11/2005 | Carron et al. |
| 2007/0222981 | A1 | * | 9/2007  | Ponsardin et al. ............ 356/301 |

FOREIGN PATENT DOCUMENTS

CN 2323371 6/1999

OTHER PUBLICATIONS

European Search Report dated Oct. 23, 2009 issued in corresponding European Application No. 09 00 8301.
Li Guoliang et al., "Applications of Raman Spectrometer in Process Monitering," www.gdchem.com 2008, vol. 35(181), pp. 106-109, 126.

* cited by examiner

*Primary Examiner* — Gregory J Toatley
*Assistant Examiner* — Iyabo S Alli
(74) *Attorney, Agent, or Firm* — Kenyon & Kenyon LLP

(57) ABSTRACT

The present invention relates to a Raman spectroscopy system that includes a detection center. The detection center includes at least one light source for outputting exciting light which excites a detected object to generate Raman scattered light, and an analysis device for obtaining the Raman spectroscopy of the detected object. The Raman spectroscopy system further includes at least one detection terminal, each of which includes at least one Raman probe that each introduces the exciting light to the detected object, collects the Raman scattered light generated by the detected object, and returns said Raman scattered light to the detection center. The present invention also relates to a method for detecting Raman spectroscopy.

13 Claims, 5 Drawing Sheets

RAMAN SPECTROSCOPY SYSTEM AND RAMAN SPECTROSCOPY DETECTION METHOD

FIELD OF THE INVENTION

The present invention relates to a Raman spectroscopy system. The present invention further relates to a method for using said system to detect the Raman spectroscopy of a detected object.

BACKGROUND INFORMATION

Light is scattered when it is irradiated on a substance. During the scattering, the wavelength of a large amount of the scattered light does not change, which is described as Rayleigh scattering, and the wavelength of a small portion of the scattered light increases or decreases, which is described as Raman scattering. A spectroscopy to which the Raman scattering corresponds is called Raman spectroscopy. Raman spectroscopy is a spectroscopy of the molecule vibration. Each substance has its own characterized Raman spectroscopy, so Raman spectroscopy can be taken as a "fingerprint" for identifying substances.

The ability of the Raman spectroscopy for identifying substances depends on the resolution of a Raman spectroscopy analyzer. The resolution relates to the focal length, the line density of the gratings and the slit width of the spectrum analyzer, etc. Generally speaking, it is necessary to use a Raman spectroscopy analyzer with a long focal length which is sufficient to increase the resolution. Then, the volume of the whole set of the analyzer system is certainly increased so that it loses portability. In addition, some optic elements in the Raman spectroscopy analyzer are expensive and they have considerably harsh demands for clearness, temperature, humidity of environment, etc., which limits the applications of Raman spectroscopy analyzers in fields like security inspection, environment inspection, chemical analysis, pharmaceutical tests, food tests, etc.

SUMMARY OF THE INVENTION

An object of the present invention is providing a Raman spectroscopy system, which allows a high-resolution and portability at the same time. Furthermore, it can meet the requirements of inspection on-sites with different environments, and it is not limited by the demands for clearness, temperature, humidity of environment, etc.

According to a first aspect of the present invention, a Raman spectroscopy system is provided. In an example embodiment of the present invention, the Raman spectroscopy system includes a detection center which has at least one light source for outputting exciting light which excites a detected object to generate Raman scattered light, and an analysis device for obtaining the Raman spectroscopy of the detected object. It further includes at least one detection terminal, each of which has at least one Raman probe, where each of the at lease one Raman probe introduces the exciting light to the detected object, collects the Raman scattered light generated by the detected object, and introduces said Raman scattered light to the detection center.

According to an example embodiment, the detection center further includes a beam splitter for splitting the exciting light outputted from the light source into multiple beams.

According to an example embodiment, the beam splitter includes one or more stages of beam splitters, between two of which a light amplifier for amplifying the exciting light is arranged.

According to an example embodiment, the detection center further includes a control device for controlling operation of the at least one light source and the analysis device and for processing the Raman spectroscopy obtained by the analysis device.

According to an example embodiment, the control device has a memory for storing a standard Raman spectroscopy database, where, when the control device is processing the Raman spectroscopy obtained by the analysis device, the control device compares said Raman spectroscopy of the detected object with a standard Raman spectroscopy read from the memory to determine whether said detected object contains a substance against a provision.

According to an example embodiment, the detection center further includes: a convertor for converting the Raman spectroscopy and transmitting the converted Raman spectroscopy to the control device; and a communication device for transmitting data between the detection center and the at least one detection terminal.

According to an example embodiment, the control device transmits the comparison results to the respective detection terminals via the communication device.

According to an example embodiment, the at least one detection terminal further includes a controller for receiving a detection instruction to control the at least one Raman probe, and a communication device for transmitting data between the detection center and the detection terminal.

According to an example embodiment, the communication device is a wired communication device or a wireless communication device.

According to an example embodiment, the detection center further includes a coupling device for coupling the exciting light from the light source to the at least one Raman probe and transmitting the Raman scattered light from the at least one Raman probe to the analysis device.

According to another aspect of the present invention, a method for detecting Raman spectroscopy of a detected object is provided. In an example embodiment of the present invention, the method includes steps of: a) controlling at least one light source to allow said light source to emit exciting light; b) controlling at least one detection terminal to allow at least one Raman probe in the at least one detection terminal to irradiate said excited light on the detected object, and collect Raman scattered light of the detected object; and c) analyzing said Raman scattered light to obtain a Raman spectroscopy of the detected object.

According to an example embodiment, the method further includes d) comparing the Raman spectroscopy of the detected object with a standard Raman spectroscopy to determine whether the detected object contains a substance against a provision.

According to an example embodiment, step b) includes: 1) automatically checking whether the at least one Raman probes is connected to a light amplifier; 2) if so, checking whether said light amplifier is activated, and if not, activating said light amplifier; 3) controlling the at least one Raman probe to automatically check whether the light source is turned on, and if it is not, turning on the light source; and 4) irradiating the exciting light from the light source on the detected object and collecting the Raman scattered light of the detected object.

According to an example embodiment, the method further includes e) transmitting the comparison results of the respective detection terminals to their own detection terminals.

The present invention solves the contradiction between the portability of the Raman spectroscopy analyzer and its resolution, because the requirement on a high resolution in the prior art leads to a rather large volume of a conventional Raman spectroscopy analyzer so that it is hard to be carried. However, the analysis of Raman spectroscopy is completed in the detection center in the present invention, so it can meet the requirement on the high resolution. At the same time, detection with multiple probe heads in parallel makes the present system possess portability, because the Raman probes are easily moved.

DETAILED DESCRIPTION

Figure 1:
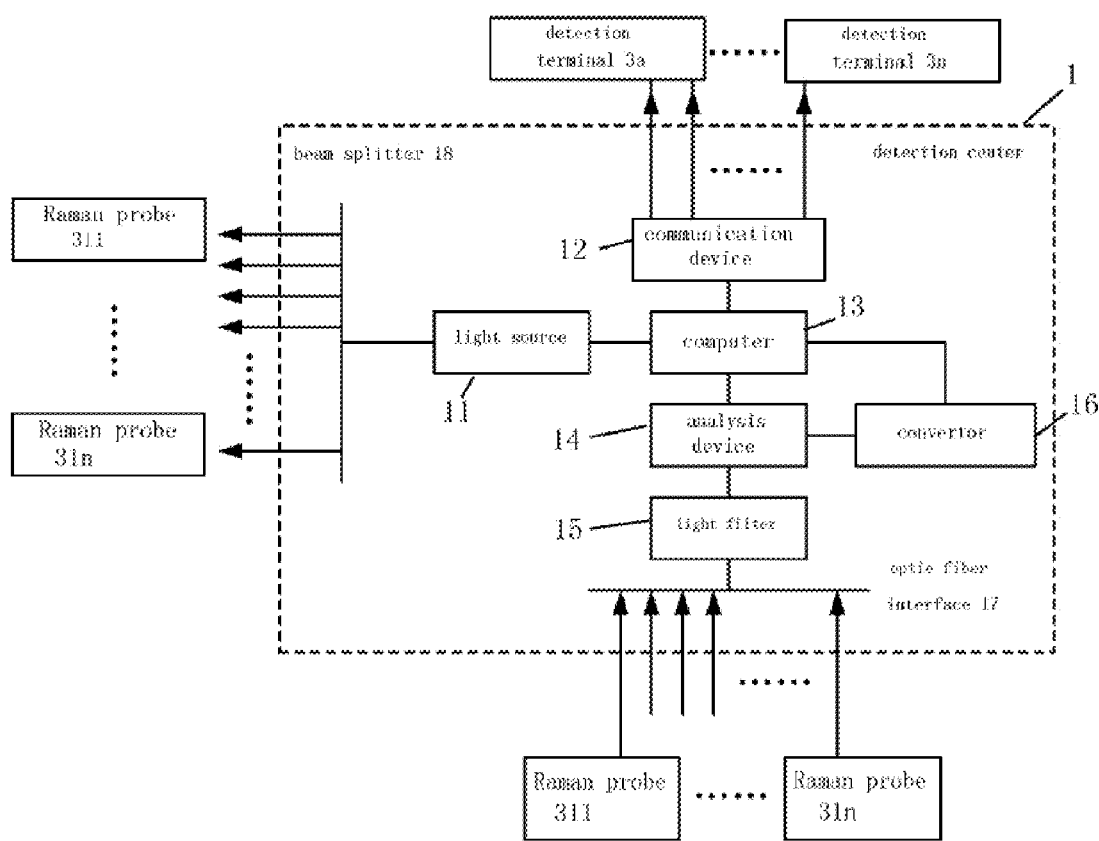
FIG. 1 is a diagram of a Raman spectroscopy system according to an example embodiment of the present invention.

FIG. 1 is a diagram of a first example embodiment of a Raman spectroscopy system of the present invention. The Raman spectroscopy system includes a detection center 1 and a plurality of detection terminals, each of which includes one or more Raman probes 311 ... 31n. The detection center 1 may be positioned in a clean and air-conditioned room at places like airports, stations, customs, buildings, stadiums, prisons, courts, etc. The Raman probes may be positioned at many different locations separated from the detection center 1 for detecting detected objects at different locations, or detecting different parts of the same object to be detected. These Raman probes may be several to hundreds of meters apart from each other.

In FIG. 1, the detection center 1 mainly includes a light source 11, a computer 13, an analysis device 14, an optic fiber interface 17, and a beam splitter 18. The light source 11 emits the exciting light for exciting the sample to be detected to generate Raman scattered light. In principle, any light source capable of providing exciting light with a narrow linewidth and a stable frequency and power can be used in the present invention. In this example, a laser having an output wavelength of 785 nm and an output power of 100 mW is used as the light source 11, whose outputted light is split by the beam splitter 18. If the light intensity of such a light source 11 is insufficient, a plurality of lasers may be arranged as the light source, and/or a light amplifier is arranged before or behind the beam splitter 18. The beam splitter 18 splits the exciting light from the light source 1 into a plurality of light beams which are coupled to the Raman probes 311 ... 31n in the detection terminals via optic fibers or via free space if necessary. These Raman probes 311 ... 31n respectively collect the Raman scattered light generated by the detected object under the radiation of the exciting light, and transmit the Raman scattered light back to the detection center 1 via the optic fiber interface 17. Stray light in the Raman optic signals collected by each Raman probe 311 ... 31n are preferably filtered by a light filter 15 and then the Raman scattered light are transmitted back to an analysis device to obtain the Raman spectroscopy of the detected object. According to an example embodiment, the analysis device 14 is the spectroscopy analyzer 14. The light filter 15 may be selected in accordance with the light source 11. In this embodiment, a notch filter having a center wavelength of 785 nm is used as the light filter 15. The Raman spectroscopy of the detected object obtained by the analysis device 14 is transmitted to the convertor 16 to convert the Raman scattered light to an electrical signal. The electrical signal is sent to the computer 13 to be processed. In this example, the convertor 16 is for example a 1024×256 CCD (Charge Coupled Device).

The computer 13, as the control device, is installed with software modules for controlling the light source 11 and the analysis device 14 and for performing a pattern recognition, and has a memory for storing a standard Raman spectroscopy database (not shown) and a monitor for displaying results (not shown). When the computer 13 receives the Raman spectroscopy of the detected object from the convertor 16, it reads the standard Raman spectroscopy from the memory and compares the Raman spectroscopy of the detected object with the standard Raman spectroscopy. If the comparison result indicates that the detected object comprises particular substances as stored in the standard Raman spectroscopy database which do not conform to relevant provisions, such as drugs and explosives in the field of security inspection, unsafe foods in the field of food safety, harmful substances in the field of environment inspection, etc., the computer 13 will generate an alerting signal. No matter whether the detected object contains substances against regulations or not, the computer 13 shows the detection result on the display device, and meanwhile, it can select to display the Raman spectroscopy of each detected object. No matter whether the detected object contains substances against regulations or not, the computer 13 will always transmit the detection results of each detected object to their respective detection terminals 3a ... 3n via a communication device 12, and their respective detection terminals 3a ... 3n will display the detection results. The communication device 12 may be wired, individually disposed or disposed together with the optic fibers, or may be wireless.

Figure 2:
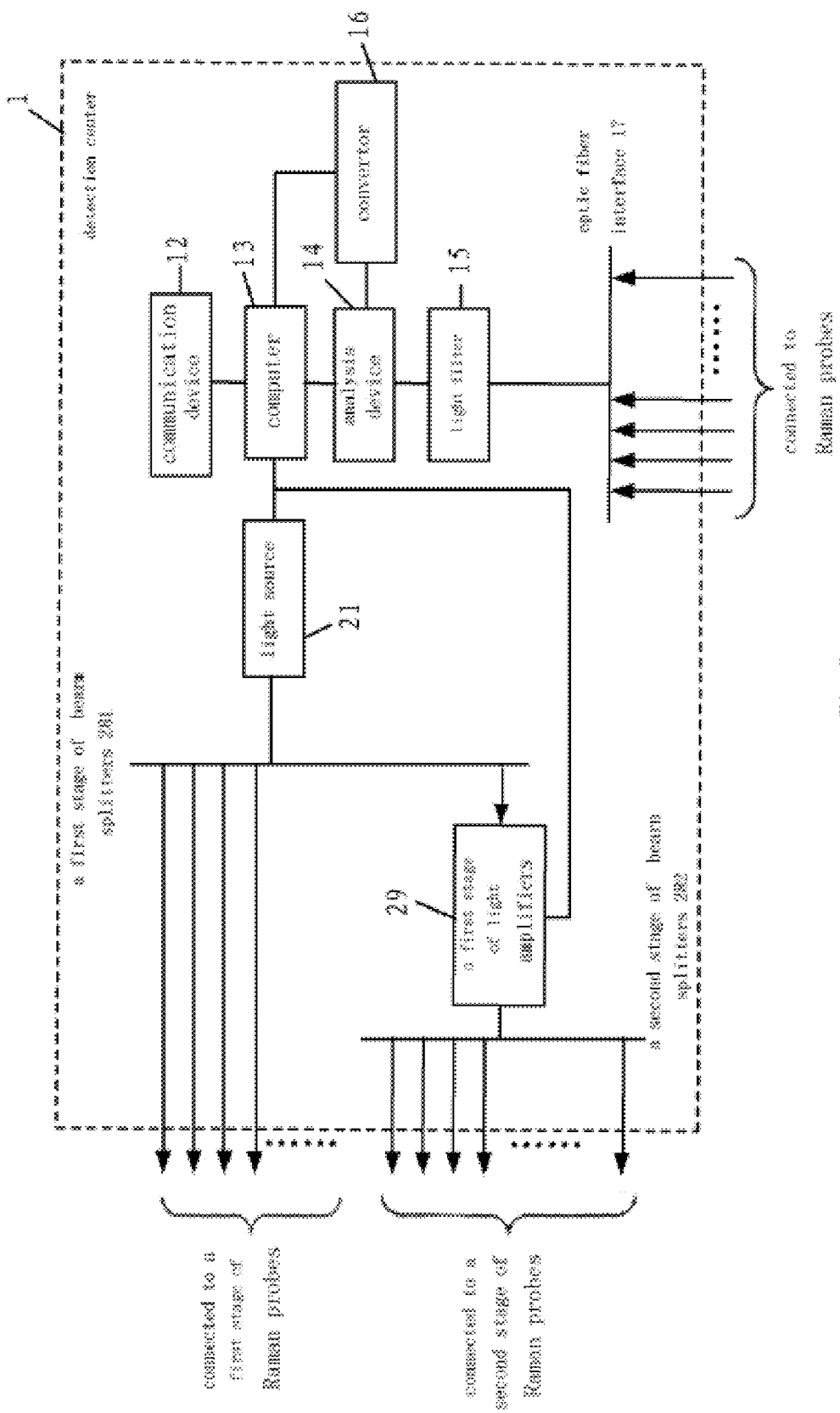
FIG. 2 shows a diagram of a Raman spectroscopy system according to a second embodiment of the present invention.

FIG. 2 shows a diagram of a second embodiment of the Raman spectroscopy system of the present invention. The features of the second embodiment are basically the same as those of the first embodiment of the Raman spectroscopy system of the present invention, except that in this embodiment the light emitted by a light source 21 undergoes splitting multiple times. The output power of the light source 21 is usually comparatively limited, so the number of the light beams obtained by the splitting of a first stage of beam splitters 281 is usually not more than 10. If it is necessary to couple more Raman probes, one or more light beams of the first stage of beam splitters 281 can be outputted and transmitted to first stage light amplifiers 29. After being amplified, one or more amplified beam outputs are transmitted to a second stage of beam splitters 282. If further Raman probes need coupling, one or more light beams of the second stage of beam splitters 282 can be outputted and transmitted to a second stage of light amplifiers. After being amplified, one or more amplified beam outputs are transmitted to a third stage of beam splitters etc.

In general, in the system configuration of splitting for n (n≧2) times of the present embodiment: the beam splitters connected to the light source are called the first stage of beam splitters; the beam splitters connected to the first stage of beam splitters via a light amplifier are called the second stage of beam splitters; the beam splitters connected to the second stage of beam splitters via a light amplifier are called the third stage of beam splitters, etc.; Raman probes connected to the ith ($1 \leq i \leq n$) stage of splitters are called the ith stage of Raman probes; Raman probes connected to the ith ($1 \leq i \leq n$) stage of light amplifiers are called the (i+1)th stage of Raman probes; light amplifiers connected to the ith ($1 \leq i \leq n$) stage of splitters are called the ith stage of light amplifiers.

The power of the incident light on each Raman probe may be the same, or may be different.

By using one or more stages of beam splitters, the Raman system of the present invention is applicable to operations of multiple tasks, namely more than one Raman probe working simultaneously. The work flow of the Raman probes in this case will be described in the following.

Figure 3:
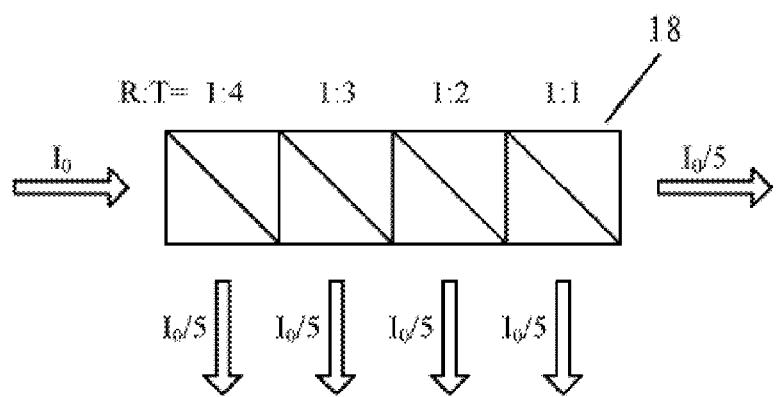
FIG. 3 shows beam splitters according to an example embodiment of the present invention.

FIG. 3 shows a diagram of the beam splitter 18 in an example embodiment of the present invention. In the figure, the beam splitter 18 evenly splits light 10 from the light source into five beams. At the same time, it illustrates the ratio of the reflectivity to transmissivity R: T.

Figure 4:
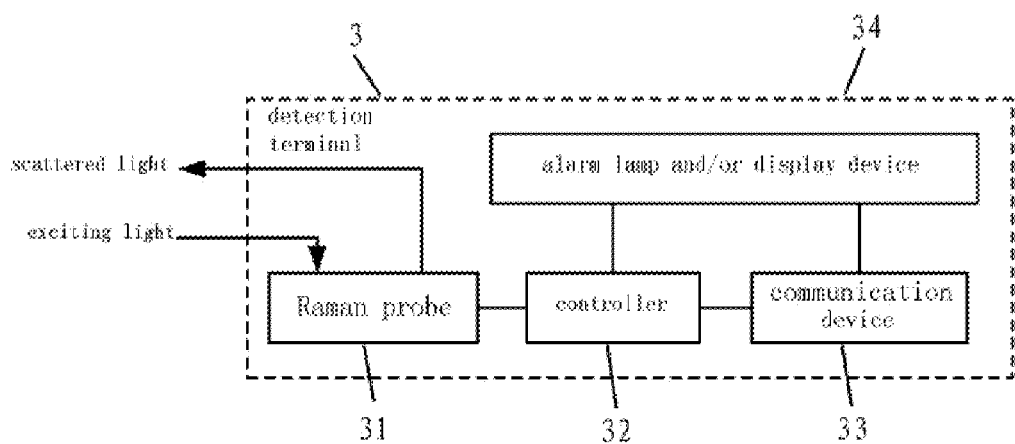
FIG. 4 shows detection terminals according to an example embodiment of the present invention.

FIG. 4 illustrates a diagram of the detection terminal 3 according to an example embodiment of the present invention. The detection terminal 3 includes one or more Raman probes 31, a controller 32, a communication device 33, an alarm lamp and/or display device 34. The Raman probe 31 receives the exciting light from light source of the detection center 1, irradiates said exciting light onto the detected object through the light path inside the Raman probe 31, collects the light scattered by the detected object, and transmits the collected scattered light to the detection center 1 as illustrated in FIG. 1 or 2. The detailed configuration of the Raman probe 31 will be discussed later. When there is one Raman probe 31, it can carry out a scanning detection on the detected object by detecting more than one point. If there are a plurality of Raman probes 31, the plurality of Raman probes 31 are able to simultaneously detect different portions of the same object to be detected, or able to carry out the scanning detection on said detected object. That is to say, each of the plurality of Raman probes detects more than one point. The plurality of Raman probes are also able to detect different detected objects. The controller 32 controls the Raman probe 31, and controls the alarm lamp and display device 34. In one example, an operator may issue an instruction for a detection to the controller 32 with a detection button on an operation panel (not shown) of the detection terminal 3. In another example, the operator may close the Raman probes 31 with the controller 32. On the other hand, through the communication device 33, the controller 32 also receives the instructions and the detection results issued and transmitted via the communication devices of the detection center 1, and displays said detection results on the alarm lamp and display device 34. The detection results are made by each of the Raman probes 31 of the detection terminals 3. The communication device 33 can be carried out in the same way as the communication devices in the detection center 1 in FIGS. 1 and 2.

Figure 5:
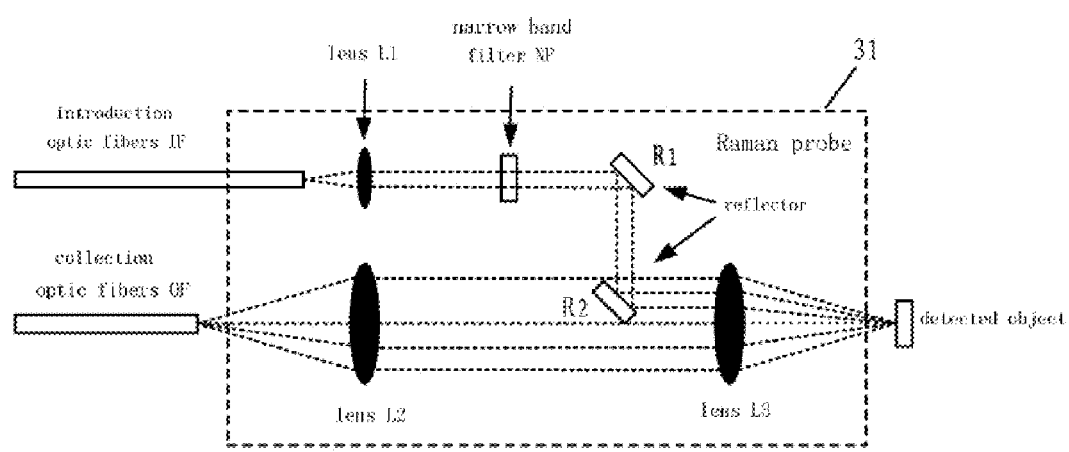
FIG. 5 shows a detailed configuration of Raman probes in the detection terminals according to an example embodiment of the present invention.

FIG. 5 shows a detailed configuration of a Raman probe 31 in the detection terminal according to an example embodiment of the present invention. The Raman probe 31 includes an introduction light path for the exciting light and a collection path for the scattered light. In the introduction light path for the exciting light, the exciting light received from the detection center 1 through introduction optic fibers IF passes, one by one, a lens L1, a narrowband filter NF, two reflectors R1 and R2, and a lens L3 to be focused on the detected object. The narrowband filter NF is used for cleaning up the exciting light to ensure that the exciting light irradiated on the detected object has good monochromaticity. If the intensity of the exciting light received by the Raman probes 31 is not sufficient, a light amplifier can be set between the introduction optic fibers IF and the lens L1. With the function of the exciting light, the detected object generates Raman scattered light which passes in the collection light path through the lens L3 and a lens L2 to enter collection optic fibers OF, and is finally transmitted to the detection center 1. Said collection light path of the scattered light may further include optic elements such as a notch filter, a long wave-pass filter, a dichroic mirror etc. for filtering the Rayleigh scattered light.

The present invention is applicable to the operation of multiple tasks. In this case, a plurality of Raman probes can work simultaneously.

Figure 6:
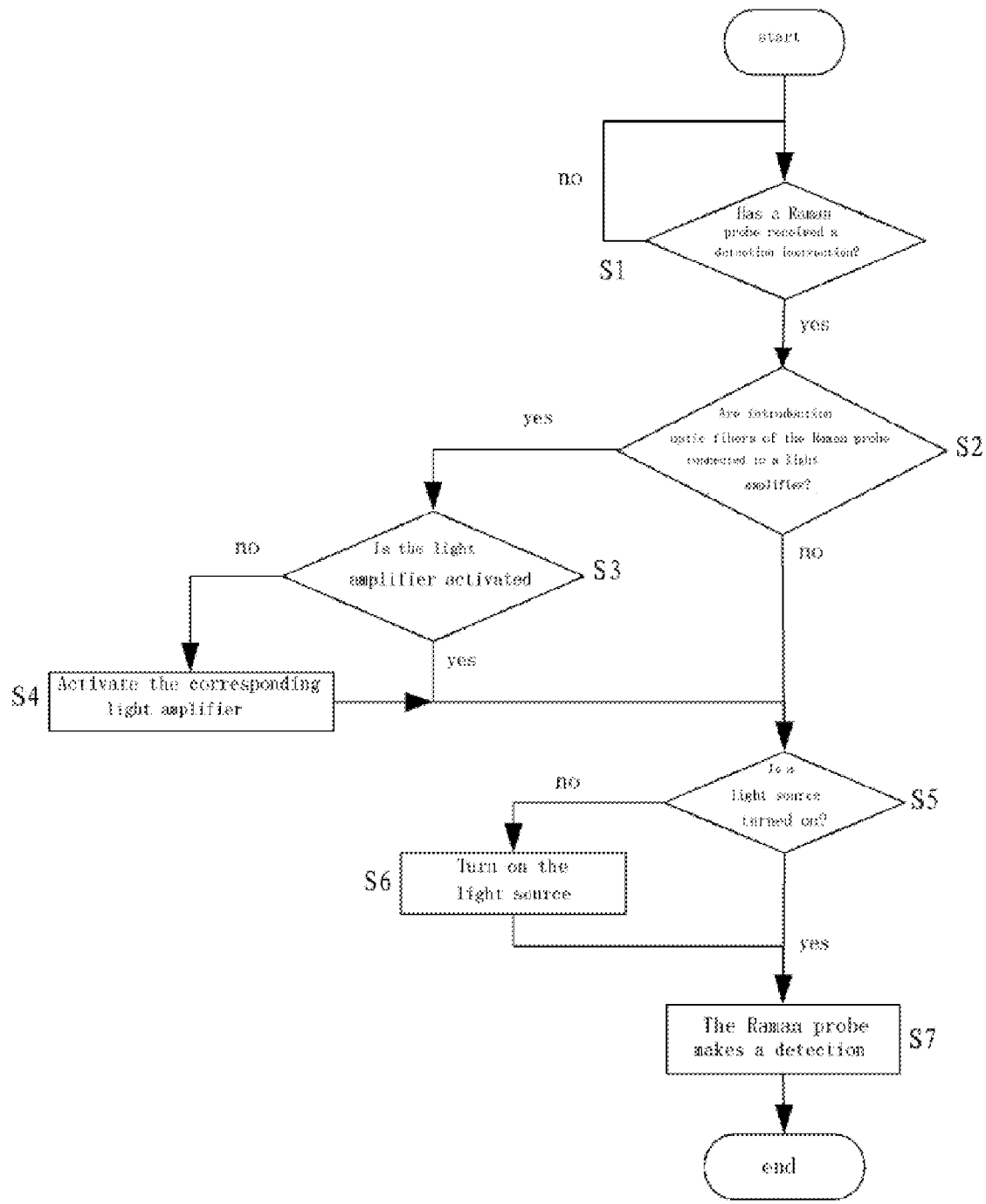
FIG. 6 is a flowchart that illustrates a work flow of the Raman probes according to an example embodiment of the present invention.

FIG. 6 illustrates a work flow of the Raman probes according to an example embodiment of the present invention. The work flow starts in step S1 with determining whether the Raman probes receive a detection instruction. If not, the Raman probes will wait for the detection instruction. If yes, then in step S2, the Raman probes automatically determine whether their introduction optic fibers are connected to a light amplifier. If yes, then in step S3, the Raman probes further determine whether the light amplifier is activated. If not, the light amplifier will be activated in step S4. No matter whether the introduction optic fibers of the Raman probes are connected to the light amplifier or not, the Raman probes will check whether the light source of the detection center is turned on in step S5. If not, the light source will be automatically turned on in step S6. After receiving the exciting light from the light source, the Raman probes irradiate the detected object in step S7, and collect the Raman scattered light, as shown in FIG. 5

In general, the present invention provides a Raman spectroscopy system. Said Raman spectroscopy system includes a detection center for obtaining the Raman spectroscopy of the detected object and indentifying the detected object according to the Raman spectroscopy, and one or plural detection terminals. Said one or more detection terminals may respectively include one or more Raman detection heads, each of which introduces the exciting light to the detected object, collects the Raman scattered light generated by the detected object and transmits said Raman scattered light to the detection center to obtain the Raman spectroscopy thereof. The Raman spectroscopy system of the present invention can achieve the detection of Raman spectroscopy with multiple probe heads in parallel and a high resolution. As Raman probes are easily moved, this system has the advantage of portability.

Those skilled in the art can appreciate from the foregoing description that the present invention may be implemented in a variety of forms, that the various embodiments may be implemented alone or in combination, and that the above described example embodiments are not used for limiting the present invention. Therefore, while the embodiments of the present invention have been described in connection with particular examples thereof, the true scope of the embodiments of the present invention should not be so limited since other modifications will become apparent to the skilled practitioner upon a study of the drawings, specification, and following claims. Many duplicate and alternative solutions, including modifications, additions, permutations, and variations, will be apparent to those skilled in the art in light of the disclosed content of the present application and should fall within the protection scope of the present invention.

What is claimed is:

1. A Raman spectroscopy system, comprising:
a detection center, comprising:
a light source for outputting exciting light which excites at least one detected object to generate Raman scattered light;
an analysis device for obtaining a Raman spectroscopy of the at least one detected object; and
a plurality of stages of beam splitters;
a light amplifier for amplifying the exciting light, the light amplifier being arranged between two of the stages of beam splitters; and
a plurality of detection terminals, each of which comprises at least one Raman probe;
wherein:
the Raman probes of the plurality of detection terminals introduce the exciting light to a plurality of locations on a detected one of the at least one detected object or to a plurality of detected objects in different locations, collect the Raman scattered light generated by the detected object or the plurality of detected objects, and return said Raman scattered light to the detection center;
the plurality of beam splitters are arranged for splitting the exciting light into a plurality of light beams that are directed to the detected object of the plurality of detected objects via the Raman probes of the plurality of detection terminals.

2. The Raman spectroscopy system according to claim 1, wherein the detection center further comprises a control device configured to control operation of the light source and the analysis device and to process the Raman spectroscopy obtained by the analysis device.

3. The Raman spectroscopy system according to claim 2, further comprising a memory that stores a Raman spectroscopy database, wherein the processing of the Raman spectroscopy by the control device, includes comparing said Raman spectroscopy of the detected object or plurality of detected objects with a Raman spectroscopy read from the database to determine whether the detected object or plurality of detected objects contains a substance against a provision.

4. The Raman spectroscopy system according to claim 2, wherein the detection center further comprises:
a convertor for converting the Raman spectroscopy to an electrical signal and then transmitting the converted Raman spectroscopy to the control device; and
a communication device for transmitting data between the detection center and the detection terminals.

5. The Raman spectroscopy system according to claim 4, wherein each of the plurality of detection terminals further comprises:
a controller for receiving a detection instruction to control the respective at least one Raman probe of the respective detection terminal; and
a communication device for transmitting data between the detection center and the respective detection terminal.

6. The Raman spectroscopy system according to claim 3, wherein the control device transmits results of the comparison to the respective detection terminals via a communication device.

7. The Raman spectroscopy system according to claim 5, wherein at least one of the communication devices is a wired communication device.

8. The Raman spectroscopy system according to claim 4, wherein the communication device is a wireless communication device.

9. The Raman spectroscopy system according to claim 1, wherein the detection center further comprises a coupling device for coupling the exciting light from the light source to the Raman probes and transmitting the Raman scattered light from the Raman probes to the analysis device.

10. A method for detecting a Raman spectroscopy of a detected object, said method comprising steps of:
a) controlling a light source to emit exciting light;
b) splitting the exciting light, by a plurality of stages of beam splitters, into a plurality of light beams;
c) amplifying, by at least one light amplifier arranged between a first one of the stages of beam splitters and a second one of the stages of beam splitters, at least a part of the exciting light which is transmitted from the first stage of beam splitters to the second stage of beam splitters;
d) controlling a plurality of detection terminals, each of which comprises at least one Raman probe, so that the Raman probes in the plurality of detection terminals irradiate said plurality of light beams on a plurality of locations on a detected object or a plurality of detected objects in different locations, and collect Raman scattered light of the detected object or plurality of detected objects; and
e) analyzing said Raman scattered light to obtain the Raman spectroscopy of the detected object or plurality of detected objects.

11. The method according to claim 10, wherein step d) comprises:
1) automatically checking, for each of the Raman probes, whether the respective Raman probe is connected to a light amplifier, and, in a case where any of the Raman probes is connected to the light amplifier:
checking whether said light amplifier is activated; and
if not activated, activating said light amplifier; and
2) controlling the Raman probes to automatically check whether the light source is turned on, and, if the light source is not turned on, turning on the light source.

12. The method according to claim 10, further comprising:
f) comparing the Raman spectroscopy of the detected object or plurality of detected objects with a stored Raman spectroscopy to determine whether the detected object or plurality of detected objects contains a substance against a provision.

13. The method according to claim 12, further comprising:
g) transmitting the comparison results obtained for respective ones of the plurality of detection terminals to the respective detection terminals.

* * * * *